United States Patent
Johnson

Patent Number: 6,030,400
Date of Patent: Feb. 29, 2000

[54] ARTICULAR CARTILAGE HARVESTING KNIFE

[76] Inventor: Lanny L. Johnson, 2950 E. Mount Hope Rd., Okemos, Mich. 48864

[21] Appl. No.: 09/173,556

[22] Filed: Oct. 16, 1998

[51] Int. Cl.$^7$ ............................................. A61B 17/32
[52] U.S. Cl. ................................. 606/167; 606/170
[58] Field of Search .................... 606/167, 170; 600/564–567, 570; 30/173, 353, 356

[56] References Cited

U.S. PATENT DOCUMENTS

| | | | |
|---|---|---|---|
| 2,690,750 | 10/1954 | Steinberg | 606/167 |
| 4,340,066 | 7/1982 | Shah | 600/567 |
| 5,300,084 | 4/1994 | Johnson | 606/167 |

Primary Examiner—Michael Buiz
Assistant Examiner—William W. Lewis
Attorney, Agent, or Firm—Pillsbury Madison & Sutro LLP

[57] ABSTRACT

An articular cartilage harvesting knife is disclosed which includes a rod having an elongated slot adjacent a distal end of the rod, the slot having a major axis lying substantially along the rod's longitudinal axis. An opening is provided in a sidewall of the rod which communicates with the slot. The proximal end of the opening defines a rearwardly extending inclined plane within the rod and an edge on the outer surface of the sidewall which, when sharpened, defines a cutting edge. When cutting edge is advanced under pressure along cartilage, the cartilage is stripped and moves into the slot and opening. In one embodiment of the invention the rod is hollowed so that stripped cartilage can be drawn from the slot and opening by suction.

22 Claims, 1 Drawing Sheet

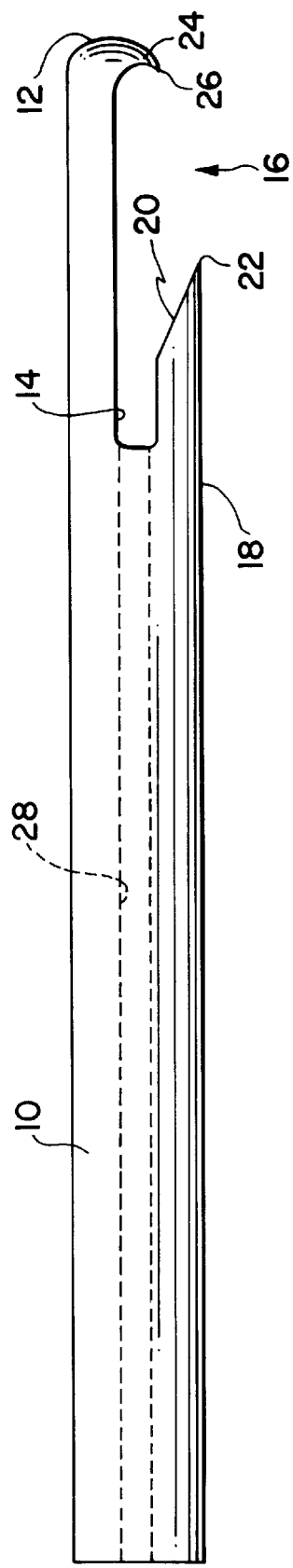

ARTICULAR CARTILAGE HARVESTING KNIFE

BACKGROUND OF THE INVENTION

1. Field of the Invention

The present invention relates to a surgical instrument for harvesting articular cartilage from a body joint.

2. Prior Art

It is customary to harvest articular cartilage tissue for pathological analysis or cell reproduction. This involves harvesting cartilage tissue from a patient and processing the tissue in a laboratory to grow a culture. If the cultured cells are then implanted in the patient, two invasions of the patient's body have occurred, each requiring general anesthesia.

It has been recognized that cartilage is available from a synovial joint that is expendable, e.g., the proximal fibular tibial joint. Typically, when harvesting cartilage from this joint, the joint is sacrificed by being completely opened during the harvesting procedure.

SUMMARY OF THE INVENTION

The present invention relates to an instrument which permits the harvesting of articular cartilage from an expandable joint without sacrificing it. If the joint is expanded and a harvesting instrument according to the present invention is used, cartilage can be harvested on an outpatient basis in a procedure requiring only local anesthesia.

The invention comprises either a solid or a hollow rod having a rounded distal end. An elongated slot is provided adjacent its distal end, the major axis of the slot lying substantially along the longitudinal axis of the rod. An opening is provided in a sidewall of the rod at the rod's distal end, the opening communicating with the slot. The proximal end of the opening is formed to lie in a rearwardly extending inclined plane so as to intersect the longitudinal axis of the rod at an acute angle. A sidewall edge formed along the inclined plane is shaped to serve as a first cutting edge. The distal end of the opening is formed to eliminate a portion of the rounded distal end of the rod and to define an optional second cutting edge where the opening meets the rod's distal end.

With the instrument just described positioned within an expanded joint and having its first cutting edge in pressure engagement with articular cartilage of the joint, proximal to distal advancement of the rod results in cartilage being stripped from the joint and deposited in the elongated slot. Such cartilage can be removed by suction when the rod is hollow. However, if the rod is solid, the slot retains the cartilage until the instrument is withdrawn from the patient.

BRIEF DESCRIPTION OF THE DRAWING

The invention now will be described with reference to the accompanying drawing which is a side elevational view of an articular cartilage harvesting knife according to the invention.

DETAILED DESCRIPTION OF PREFERRED EMBODIMENTS OF THE INVENTION

Referring to the drawing, a cylindrical metal rod 10, preferably formed of stainless steel, is rounded at its distal end 12. An elongated slot 14 is provided adjacent the distal end 12 of the rod, the major axis of the slot lying substantially along the longitudinal axis of rod 10. An opening 16 is provided in the sidewall 18 of the rod adjacent distal end 12. The opening 16 communicates with slot 14 and is formed at its proximal end with a rearwardly extending inclined plane 20 intersecting the longitudinal axis of rod 10 at an acute angle at a location intermediate the ends of slot 14. Plane 20 defines an edge 22 on the outer surface of the sidewall which is sharpened to serve as a first cutting edge. The opening 16 at its distal end eliminates a portion of the rounded distal end 12 of rod 10. Preferably, up to 50% of end 12 is eliminated. As a result, the tip 24 of end 12 is spaced from the longitudinal axis of rod 10 by distance less than the distance from the longitudinal axis to edge 22. Additionally, the intersection of opening 16 and tip 24 defines an edge 26 which optionally may be sharpened to serve as a second cutting edge.

A hollow 28 may be provided along the longitudinal axis of rod 10 intersecting slot 14. If the rod is so hollowed, the hollow permits a source of suction (not shown) to be applied to the proximal end of rod 10 to remove materials collected in the slot.

The instrument having been disclosed, its use in harvesting articular cartilage from a joint now will be described. It will be assumed that the harvesting source is an expendable body joint, such as the proximal fibular tibial joint. Of course, the invention can be employed in harvesting cartilage from other joints.

A short skin and subcutaneous incision over the anterior surface of the joint is made to expose, but not open, the joint. The joint is expanded either by being distended with fluid in customary fashion or by being spread utilizing an instrument of the type disclosed in my copending application, entitled "Rotatable Retractor", filed concurrently herewith. Penetration into the joint is then made with a solid obturator, the portal so formed serving as the harvesting knife's access to the joint. As the knife enters the joint, edge 22 is brought into pressure engagement with the cartilage to be harvested. Advancing the knife in a proximal to distal direction results in cartilage being stripped from the joint, the stripped cartilage moving along inclined plane 20 to be received within the slot 14. When the knife is moved in the distal to proximal direction, and if edge 26 is sharpened, 26 severs any remaining strip of cartilage formed by edge 22. If rod 10 is provided with a hollow 28 and suction is applied to the proximal end of the rod, harvested cartilage is removed from the slot 14 along hollow 28 to a collector (not shown). If no hollow is provided in the rod, the harvested cartilage is stored in slot 14 and opening 16 until the knife is completely withdrawn from the patient.

The rounded distal end 12 of rod 10 blunts the rod and prevents penetration of the rod through the far side of the joint.

The elimination of a portion of the distal end 12 facilitates engagement of the first edge 22 with the cartilage so as permit cartilage to be stripped by edge 22. When the knife is withdrawn, downward pressure exerted at the distal end 12 of the rod permits optional cutting edge 26 to sever any remaining cartilage strip formed by edge 22.

The instrument which has been described can be used in conventional open surgical procedures or under arthroscopic control.

What is claimed is:

1. A cartilage harvesting knife comprising:
   a rod having a longitudinal axis;
   an elongated slot provided in said rod adjacent a distal end of the rod, said slot having a major axis lying substantially along the longitudinal axis of the rod;

an opening provided in a sidewall of said rod adjacent the rod's distal end, said opening communicating with said slot and defining, along a proximal end of the opening:
   (a) an inclined surface in the sidewall extending rearwardly and lying in a plane which intersects the longitudinal axis of the rod at an acute angle; and
   (b) an edge of said inclined surface, located on an outer surface of the sidewall, which is sharpened to create a cutting edge.

2. A cartilage harvesting knife according to claim 1, wherein said distal end of the rod is rounded.

3. A cartilage harvesting knife according to claim 1, wherein said rod is hollowed along its longitudinal axis from a proximal end of the rod to said slot.

4. A cartilage harvesting knife according to claim 3, wherein said distal end of the rod is rounded.

5. A cartilage harvesting knife according to claim 1, wherein said opening eliminates a portion of the distal end of the rod.

6. A cartilage harvesting knife according to claim 5, wherein said opening and the distal end of the rod intersect to define a further edge which is sharpened to provide an additional cutting edge.

7. A cartilage harvesting knife according to claim 6, wherein said distal end of the rod is rounded.

8. A cartilage harvesting knife according to claim 7, wherein said rod is hollowed along its longitudinal axis from a proximal end of the rod to said slot.

9. A cartilage harvesting knife according to claim 7, wherein up to 50% of the distal end of the rod is eliminated by the opening.

10. A cartilage harvesting knife according to claim 5, wherein said distal end of the rod is rounded.

11. A cartilage harvesting knife according to claim 10, wherein said rod is hollowed along its longitudinal axis from a proximal end of the rod to said slot.

12. A cartilage harvesting knife according to claim 10, wherein up to 50% of the distal end of the rod is eliminated by the opening.

13. A cartilage harvesting knife according to claim 1, wherein said inclined surface intersects the slot intermediate opposite ends of the slot.

14. A cartilage harvesting knife according to claim 13, wherein said distal end of the rod is rounded.

15. A cartilage harvesting knife according to claim 13, wherein said rod is hollowed along its longitudinal axis from a proximal end of the rod to said slot.

16. A cartilage harvesting knife according to claim 15, wherein said distal end of the rod is rounded.

17. A cartilage harvesting knife according to claim 13, wherein said opening eliminates a portion of the distal end of the rod.

18. A cartilage harvesting knife according to claim 17, wherein said opening and the distal end of the rod intersect to define a further edge which is sharpened to provide an additional cutting edge.

19. A cartilage harvesting knife according to claim 17, wherein said distal end of the rod is rounded.

20. A cartilage harvesting knife according to claim 17, wherein said rod is hollowed along its longitudinal axis from a proximal end of the rod to said slot.

21. A cartilage harvesting knife according to claim 19, wherein said distal end of the rod is rounded.

22. A cartilage harvesting knife according to claim 20, wherein up to 50% of the distal end of the rod is eliminated by the opening.

* * * * *